United States Patent [19]

Mahajan et al.

[11] Patent Number: 4,613,623
[45] Date of Patent: Sep. 23, 1986

[54] LOW TEMPERATURE SYNTHESIS OF METHYL FORMATE

[75] Inventors: Devinder Mahajan, Selden; William A. Slegeir, Hampton Bays; Richard S. Sapienza, Shoreham; Thomas E. O'Hare, Huntington Station, all of N.Y.

[73] Assignee: The United States of America as represented by the United States Department of Energy, Washington, D.C.

[21] Appl. No.: 757,981

[22] Filed: Jul. 23, 1985

[51] Int. Cl.[4] ............................................. C07C 27/06
[52] U.S. Cl. .................................. 518/700; 518/714
[58] Field of Search ........................................ 518/700

[56] References Cited

U.S. PATENT DOCUMENTS

| | | |
|---|---|---|
| 3,493,610 | 2/1970 | Coffield . |
| 3,716,609 | 2/1973 | Lynn et al. . |
| 3,772,380 | 11/1973 | Poulik et al. . |
| 3,856,856 | 12/1974 | Nozaki . |
| 4,133,963 | 1/1979 | Holmes . |
| 4,134,912 | 1/1979 | Naglier et al. . |
| 4,151,190 | 4/1979 | Murchison et al. . |
| 4,252,741 | 2/1981 | Porcelli et al. . |
| 4,408,069 | 10/1984 | Doyle . |

FOREIGN PATENT DOCUMENTS

| | | |
|---|---|---|
| WO84/00360 | 2/1984 | PCT Int'l Appl. . |
| 1047408 | 11/1966 | United Kingdom . |

OTHER PUBLICATIONS

BNL Report 36282, Slegeir et al, Methanol Synthesis at Low Temperature, May 8-10, 1984.
Tonner et al, Journal of Molec. Catalysis, 18, 215-222, (1983).

*Primary Examiner*—Howard T. Mars
*Attorney, Agent, or Firm*—Margaret C. Bogosian; James W. Weinberger; Judson R. Hightower

[57] ABSTRACT

A gas reaction process for the preferential production of methyl formate over the co-production of methanol wherein the reactant ratio of $CO/H_2$ is upgraded and this reaction takes place at low temperatures of 50°–150° C. and moderate pressures of $\geq 100$ psi.

3 Claims, No Drawings

LOW TEMPERATURE SYNTHESIS OF METHYL FORMATE

The U.S. Government has rights in this invention pursuant to Contract No. DE-AC02-76CH00016, between the U.S. Department of Energy and Associated Universities Inc.

BACKGROUND OF THE INVENTION

The present invention is a process for the preferential production of methyl formate by the catalyzed gas reaction of carbon monoxide and hydrogen. This may be expressed as the reaction of synthesis gas under influence of a homogeneous catalyst to carbonylate and produce methyl formate. This reaction is conducted under relatively low temperature, 50°–150° C., and relatively low pressure, ≧100 psi.

Two predominantly superior gas reactions are involved in the catalyzed synthesis gas reaction and the equations for these two reactions are set out below:

$$2\,CO + 2H_2 \rightarrow HCOOCH_3 \text{ (methyl formate)} \qquad \text{EQ. I}$$

$$CO + 2H_2 \rightarrow CH_3OH \text{ (methanol)} \qquad \text{EQ. II}$$

The purpose of the instant process is to so control the reaction conditions that the production of methyl formate will be preferred to that of methanol, so that methyl formate is the predominant end product produced directly from synthesis gas and not through a methanol intermediate. In the present reaction (I) given an input ratio of about 1:1 for carbon monoxide over hydrogen, the output of methyl formate may range up to 50 percent when calculated in the ratio of methyl formate to methanol. The catalyst utilized here is an alkoxide catalyst, produced from the reaction of an alkali metal hydride with a tertiary alcohol, which is combined with a metal carbonyl. More specifically, the catalyst consists of the complex reducing agent of the formula XH—ROH—M(OAc)$_2$ wherein X is an alkali metal, M is selected from the group consisting of Ni, Pd, and Co and R is a lower alkyl group containing 1–6 carbon atoms, which is incorporated into a system where the second component in the system consists of a metal carbonyl selected from the group VI metals (Cr, Mo, W), with Mo(CO)$_6$ being preferred. This system thus contains the complex reducing agent capable of activating hydrogen for reducing carbonyl bonds, as well as the metal carbonyl which is capable of activating carbon monoxide. The catalyst system may also be designated as XOR/M(CO)$_n$ wherein X, R and M are as defined above. A preferred combination utilizes potassium t-amyl alkoxide or t-butoxide with Ni(CO)$_4$ in a solvent such as tetrahydrofuran.

An overall equation expressing the present invention is $$2CO + 2H_2 \xrightarrow[50-150°\,C.]{\text{Homogeneous catalyst}} HCOOCH_3 + CH_3OH$$

≧100 psi syngas and the theory of the gas reaction is as follows. The reaction may be described as a method for converting synthesis gas directly into methyl formate at low temperature and pressures utilizing the above described catalyst system. In a typical run where the reactor contains the homogeneous catalyst and said catalyst is pressurized with synthesis gas, co-production of methyl formate and methanol takes place, and a more positive ratio of methyl formate to methanol can be achieved by upgrading the CO in the CO/H$_2$ ratio in the feed synthesis gas.

In this reaction methyl formate may be synthesized in a one step process directly from synthesis gas and also there may be co-production of methyl formate and methanol which can be realized in one pot with a ratio of the two controllable by varying the CO/H$_2$ ratio in the feed gas. All of this is accomplished at low temperature, 50°–150° C., and pressures of ≧100 psi.

DETAILED DESCRIPTION OF THE INVENTION

The present process describes catalyst formulations and conditions that allow for the synthesis of significant yields of methyl formate directly and in one step from CO and H$_2$ at modest temperatures. Although it is realized that conventional catalysts for methanol synthesis afford traces of methyl formate, the high temperatures involved, generally >250°, needed for adequate rates, and the high hydrogen partial pressures needed for acceptable conversion, both suppress methyl formate formation in favor of methanol.

In the present process methyl formate is directly synthesized from synthesis gas in one step and this synthesis dynamically favor the synthesis of methyl formate and lower partial pressures of hydrogen can be used without severe operational penalties.

Specifically, in the operation of the present process, a homogeneous catalyst system is used. This catalyst system is prepared as set out in the two equations noted below:

$$XH + ROH \rightarrow XOR \text{ (alkoxide component)} \qquad \text{EQ. III}$$

$$XH + M\,(OAc)_2 + ROH \rightarrow XH\text{—}ROH\text{—}M(OAc)_2 \qquad \text{EQ. IV}$$

In the above two equations, X, R and M are as defined above. The catalyst component resulting from equation IV is then combined with the metal carbonyl to produce the catalyst system.

The utilization of the catalyst system prepared when X in potassium allows more rapid production and the alkoxide appears to be more soluble. The catalyst is solubilized in a solvent and utilized as a homogeneous liquid catalyst in the gas reaction. Any convenient solvent capable of solubilizing the metal metal and alkali metal components of the catalyst may be utilized. A preferred solvent is tetrahydrofuran and other utilizable solvents are 2-methyl tetrahydrofuran, 1,2-diethoxyethane, 1,2-dimethoxyethane, and methyl formate.

Preferably a synthesis gas which has a ratio of about 1:1 hydrogen and carbon monoxide is utilized as the feed gas and temperatures of conversion of 50°–150° C. and pressure of at least 100 psi are utilized. The production of methyl formate by this process is up to a 50% ratio with the co-production of methanol.

EXAMPLE 1

To a stirred suspension of sodium hydride (60 mmols), and dry nickel acetate (10 mmols) in 25 ml tetrahydrofuran was added dropwise, at 45° C. and under an argon atmosphere, a solution of tertiary amyl alcohol (20 mmols) in 5 ml tetrahydrofuran. Stirring was continued for 2 hrs. during which time the liquid became black. An additional portion of tertiary amyl alcohol (32 mmol) was then added to neutralize the remaining sodium hydride, and the mixture was allowed to return to room temperature.

A non-pyrophoric black suspension resulted which was then transferred under argon to a Parr Model 4561 300 ml stirred pressure reactor containing 1.3 g molybdenum hexacarbonyl (5 mmol), to which an additional 70 ml tetrahydrofuran was added. After flushing with hydrogen, the reactor was charged with 300 psi of a mixture of 33% carbon monoxide in hydrogen and heated to 100° C. The pressure decreased during the run due to syngas consumption. During this time the catalyst precursor was "conditioned", that is, converted to the active catalyst. After 2 hr, the pressure had decreased to 50 psi and the reactor was cooled. It was then pressurized with 2:1 ($H_2$:CO) syngas, heated again to 100° C. and similar gas consumption was observed. After a third charging and heating cycle, the reactor was cooled and a sample was withdrawn and analyzed. The predominant products were methyl formate and methanol. The yield of desired methyl formate product was increased by increasing CO concentration in the feed synthesis gas to about 1:1 ($H_2$:CO).

EXAMPLE 2

Methyl formate was produced within a few minutes when a reactor containing nickel tetracarbonyl [Ni(CO)$_4$] and an alkoxide base (alkoxide base is usually prepared by the reaction of tertiary alcohols with alkali metal hydrides) dissolved in a solvent, for example, tetrahydrofuran, was pressurized with 1:1 ($H_2$:CO) synthesis gas and heated to 50°–150° C.

EXAMPLE 3

When an alkoxide base, prepared by reacting alkali metal with tertiary alcohol, was loaded into a reactor along with Ni(CO)$_4$ and the reactor was heated between 50°–150° C. after pressurizing with synthesis gas, synthesis gas was consumed within minutes with concomitant formation of methyl formate and methanol.

EXAMPLE 4

When any of the above catalysts described in Examples 1–3 were used at 100° C., methyl formate to methanol ratio between 0–50% was obtained, depending on the CO/$H_2$ ratio in feed synthesis gas. Methyl formate yield was further increased by lowering the reaction temperature.

EXAMPLE 5

Using catalysts discussed in Examples 1–3, pure methyl formate was synthesized simply by distilling the final solution from such reactions.

We claim:

1. In the simultaneously occuring gas reactions (a) $2CO+2H_2\rightarrow HCOOCH_3$ and (b) $CO+2H_2\rightarrow CH_3OH$ catalyzed by a catalyst system composed of a complex reducing agent of the formula XH—ROH—M(OAc)$_2$ wherein X is an alkali metal, M is selected from the group consisting of Ni, Pd or Co and R is a lower alkyl group containing 1–6 carbon atoms and a Group VI metal carbonyl, the improvement which favors driving the reaction to the right in (a) which comprises using said catalyst system as a homogeneous liquid phase catalyst and pressurizing the system which synthesis gas containing about an equimolar amount v/v of CO to the $H_2$ reactant so that the product ratio of HCOOCH$_3$/CH$_3$OH will be up to 1:1.

2. In the improved gas reaction of claim 1, utilizing as said catalyst system a complex reducing agent component wherein X is potassium and M is nickel.

3. In the improved gas reaction of claim 1, utilizing said complex reducing agent wherein M is Ni, R is tertiary amyl and the Group VI metal carbonyl is molybdenum hexacarbonyl.

* * * * *